United States Patent
Young et al.

(10) Patent No.: US 12,200,606 B2
(45) Date of Patent: *Jan. 14, 2025

(54) IMPLANTABLE MEDICAL DEVICE WITH SECURE CONNECTION TO AN EXTERNAL INSTRUMENT

(71) Applicant: Pacesetter, Inc., Sylmar, CA (US)

(72) Inventors: Chaowen Young, Cupertino, CA (US); Yongjian Wu, Saratoga, CA (US); Jyoti Bhayana, Milpitas, CA (US); Samir Shah, Valencia, CA (US); Reza Shahandeh, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 580 days.

This patent is subject to a terminal disclaimer.

(21) Appl. No.: 16/953,461

(22) Filed: Nov. 20, 2020

(65) Prior Publication Data

US 2021/0076312 A1 Mar. 11, 2021

Related U.S. Application Data

(60) Division of application No. 16/701,806, filed on Dec. 3, 2019, now Pat. No. 10,880,826, which is a (Continued)

(51) Int. Cl.
*H04W 76/10* (2018.01)
*A61N 1/372* (2006.01)
(Continued)

(52) U.S. Cl.
CPC ........ *H04W 48/16* (2013.01); *A61N 1/37223* (2013.01); *A61N 1/37252* (2013.01); *H04W 76/14* (2018.02)

(58) Field of Classification Search
CPC ..... H04W 48/16; H04W 76/14; H04W 12/00; H04W 4/80; H04W 12/00407;
(Continued)

(56) References Cited

U.S. PATENT DOCUMENTS 9,833,628 B2  12/2017 Yoder et al.
9,844,676 B2  12/2017 Zhang et al.
(Continued)

FOREIGN PATENT DOCUMENTS

CN    108257664 A    7/2018
WO   2018156386 A1   8/2018

OTHER PUBLICATIONS

International Search Report and Written Opinion for corresponding Application No. PCT/US2019/064202 dated Feb. 20, 2020 (13 pages).

(Continued)

*Primary Examiner* — Andrew Wendell
(74) *Attorney, Agent, or Firm* — Dean D. Small; The Small Patent Law Group, LLC

(57) ABSTRACT

An implantable medical device (IMD) that includes a transceiver configured to broadcast an advertising data packet that includes a unique identifier, and to receive a scan request data packet from an external device. A memory stores program instructions, and stores an approved device list, and one or more processors are configured to execute the program instructions to identify a device identifier (ID) from the scan request data packet received, apply an advertising filter to determine if the scan request data packet is from an authorized external device based on the device ID and the approved device list, based on the determination by the advertising filter, deny transmission of a scan response data packet from the transceiver when the advertising filter determines that the scan request data packet is from an unauthorized external device, and establish a communication session with an authorized external device independent of the scan request data packet.

18 Claims, 6 Drawing Sheets

Related U.S. Application Data continuation of application No. 16/227,519, filed on Dec. 20, 2018, now Pat. No. 10,582,444.

(51) Int. Cl.
*H04W 12/00* (2021.01)
*H04W 48/16* (2009.01)
*H04W 76/14* (2018.01)

(58) Field of Classification Search
CPC ... H04W 4/23; H04B 1/3816; H04B 7/18565; H04B 7/18593; A61N 1/37223; A61N 1/37252
See application file for complete search history.

(56) References Cited

U.S. PATENT DOCUMENTS

| | | | |
|---|---|---|---|
| 9,913,989 B2 | 3/2018 | Schilling et al. | |
| 9,980,140 B1 | 5/2018 | Spencer et al. | |
| 10,055,567 B2 | 8/2018 | Ulrich et al. | |
| 10,086,208 B2 | 10/2018 | Hoffman et al. | |
| 10,124,182 B2 | 11/2018 | Kivi et al. | |
| 10,201,712 B2 | 2/2019 | Yoder et al. | |
| 10,305,692 B2 | 5/2019 | Peterson | |
| 10,307,599 B2 | 6/2019 | Schilling et al. | |
| 10,493,287 B2 | 12/2019 | Yoder et al. | |
| 10,576,290 B2 | 3/2020 | Schilling et al. | |
| 10,582,444 B1 | 3/2020 | Young et al. | |
| 10,617,875 B2 | 4/2020 | Demmer et al. | |
| 10,880,826 B2 * | 12/2020 | Young | H04W 48/16 |
| 11,315,393 B1 * | 4/2022 | Zalewski | G07G 1/0072 |
| 2015/0119077 A1 | 4/2015 | Buchheim et al. | |
| 2016/0134709 A1 | 5/2016 | Savolainen | |
| 2016/0255456 A1 | 9/2016 | Lee et al. | |
| 2017/0216611 A1 * | 8/2017 | Yoder | A61N 1/37217 |
| 2017/0265080 A1 | 9/2017 | Azam et al. | |
| 2017/0312530 A1 | 11/2017 | Schilling | |
| 2018/0028827 A1 | 2/2018 | Schilling et al. | |
| 2018/0243567 A1 | 8/2018 | St. Martin et al. | |
| 2018/0243568 A1 | 8/2018 | Demmer et al. | |
| 2018/0243573 A1 | 8/2018 | Yoder et al. | |
| 2018/0243577 A1 | 8/2018 | Kivi et al. | |
| 2018/0295660 A1 | 10/2018 | Choi et al. | |
| 2020/0094062 A1 | 3/2020 | Yoder et al. | |

OTHER PUBLICATIONS

Office Action for corresponding CN Application No. 201980068949.6 dated Jan. 6, 2024 (30 pages).

* cited by examiner

IMPLANTABLE MEDICAL DEVICE WITH SECURE CONNECTION TO AN EXTERNAL INSTRUMENT

REFERENCE TO RELATED APPLICATIONS

The present application is a divisional application of, and claims priority to, United Stated application Ser. No. 16/701,806, Titled "IMPLANTABLE MEDICAL DEVICE WITH SECURE CONNECTION TO AN EXTERNAL INSTRUMENT" which was filed on Dec. 3, 2019 which is a continuation application of, and claims priority to, U.S. application Ser. No. 16/227,519, Titled "IMPLANTABLE MEDICAL DEVICE WITH SECURE CONNECTION TO AN EXTERNAL INSTRUMENT" which was filed on Dec. 20, 2018 (now U.S. Pat. No. 10,582,444, issued Mar. 3, 2020), the complete subject matter of each are expressly incorporated herein by reference in their entirety.

BACKGROUND

Embodiments of the present disclosure generally relate to device discovery systems and methods that utilize countermeasures against active scanning attacks on an implantable medical device.

An implantable medical device (IMD) is a medical device that is configured to be implanted within a patient anatomy and commonly employs one or more electrodes that either receive or deliver voltage, current or other electromagnetic pulses from or to an organ or tissue for diagnostic or therapeutic purposes. In general, IMDs include a battery, electronic circuitry, a pulse generator, a transceiver and/or a microprocessor that is configured to handle communication with an external instrument as well as control patient therapy. The components of the IMD are hermetically sealed within a metal housing. The IMD is completely enclosed within the human body. Thus, there is no means of direct interaction with an IMD, other than through wireless communication.

However, IMDs are typically built with non-replaceable batteries that limit options for communications solutions. Typically, the wireless communication is maintained utilizing a low range, low power communications platform during short periods of time. Existing communication solutions experience certain limitations regarding power consumption. For example, in some environments, current consumption or, more generally, energy usage during communication remains a concern in the implantable medical device (IMD). For a Bluetooth Low Energy (BLE) enabled IMD, current consumption by the IMD during advertising is particularly of interest as energy usage during advertising can significantly impact the IMD battery longevity.

A need remains for improved methods and devices for establishing secure communication between IMDs and external instruments that does not unduly draw upon battery energy.

BRIEF SUMMARY

In accordance with embodiments herein, an implantable medical device (IMD) that includes a transceiver configured to broadcast an advertising data packet that includes a unique identifier. The transceiver is further configured to receive a scan request data packet from an external device. A memory stores program instructions, and stores an approved device list. One or more processors are configured to execute the program instructions to identify a device identifier (ID) from the scan request data packet received, apply an advertising filter to determine if the scan request data packet is from an authorized external device based on the device ID and the approved device list, based on the determination by the advertising filter, deny transmission of a scan response data packet from the transceiver when the advertising filter determines that the scan request data packet is from an unauthorized external device, and establish a communication session with an authorized external device independent of the scan request data packet.

Optionally, the one or more processors are further configured to execute the program instructions to compare multiple device identifiers from corresponding multiple scan request data packets from corresponding multiple external devices to the approved device list, and record a log of at least a portion of the device identifiers received in scan request data packets that were not on the approved device list.

Alternatively, the transceiver is further configured to receive a connection request data packet from the authorized external device based on the unique identifier of the advertising data packet. Optionally, the one or more processors are further configured to execute the program instruction to establish the communication session with the authorized external device based on the connection request data packet from the authorized external device. Alternatively the one or more processors are further configured to execute the program instructions to, responsive to receiving a device identification request related to the connection request data packet, transmit a device identifier related to the IMD to the authorized external device. Also alternatively, the transceiver is configured to receive the connection request data packet from the authorized external instrument for a predetermined interval after broadcast of the advertising data packet. Optionally, the predetermined interval is less than ten seconds.

In another example, the IMD is one of a cardiac monitoring device, pacemaker, cardioverter, cardiac rhythm management device, defibrillator, neurostimulator, leadless monitoring device, or leadless pacemaker.

Optionally, one or more processors includes a communication control processor that operates the transceiver to communicate with the authorized external device using one or more wireless communication protocols. In one example, the one or more wireless communication protocols include a Bluetooth low energy (BLE) protocol.

In accordance with embodiments herein, a method for establishing secure communications with an implantable medical device (IMD) that includes broadcasting an advertising data packet including a unique identifier from the IMD utilizing a communication protocol. The method also includes receiving scan request data packets from external devices at a transceiver of the IMD, determining a device identifier (ID) from a scan request data packet received at the IMD, and applying an advertising filter to determine if the scan request data packet is from an authorized external device based on the device ID and an approved device list. Based on the determination by the advertising filter, transmission of a scan response data packet from the transceiver is denied when the advertising filter determines that the scan request data packet is from an unauthorized external device. The method also includes recording a log of at least a portion of the device identifiers received in scan request data packets that were not on the approved device list.

Optionally, the method includes establishing a communication session with an authorized external device independent of the scan request data packet. Additionally, the method includes receiving the advertising data packet including the unique identifier at the authorized external device, and transmitting a connection request data packet from the authorized external device based on the unique identifier of the advertising data packet. In addition, the method includes receiving the connection request data packet at the IMD from the authorized external device, and establishing the communication session between the IMD and authorized external device based on the connection request data packet. Optionally, responsive to receiving the connection request data packet, a device identifier related to the IMD is transmitted from the IMD to the authorized external device.

Alternatively, applying the advertising filter to determine if the scan request data packet is from an authorized external device based on the device ID and the approved device list includes comparing the device ID to device identifiers of authorized external devices on the approved device list. In one aspect, the only device identifier of authorized external devices on the approved device list is the unique identifier of the IMD.

In one example a communication control processor operates the transceiver of the IMD to communicate with the authorized external device using one or more wireless communication protocols. Optionally, the one or more wireless communication protocols include a Bluetooth low energy (BLE) protocol. In another example, IMD is one of a cardiac monitoring device, pacemaker, cardioverter, cardiac rhythm management device, defibrillator, neurostimulator, leadless monitoring device, or leadless pacemaker.

DETAILED DESCRIPTION

Figure 1:
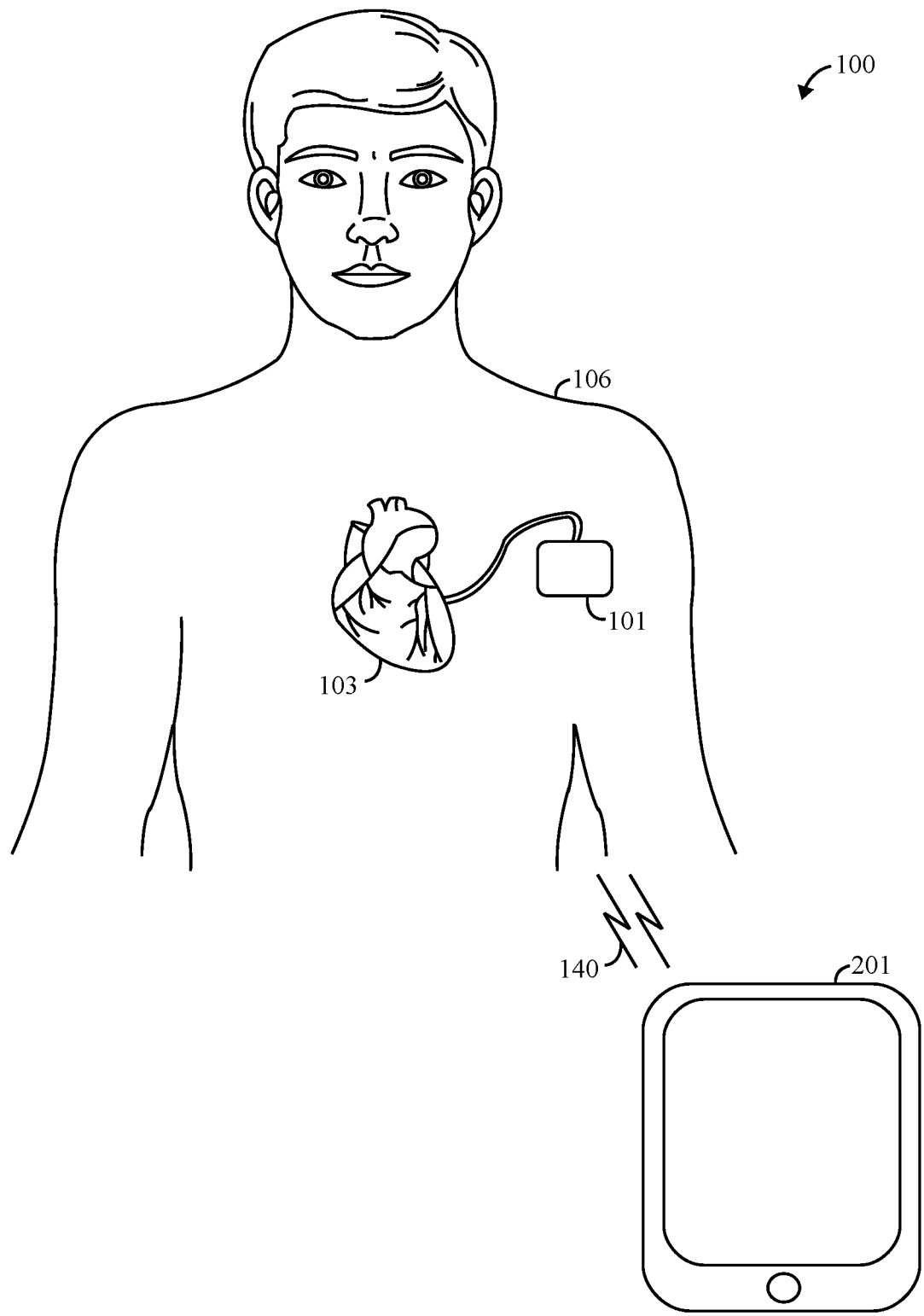
FIG. 1 illustrates a simplified block diagram of a communication system operated in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Embodiments herein provide methods and systems that address the main factors affecting advertising current consumptions in a BLE-enabled IMD, namely a total amount of time that a transceiver in the IMD is active. The amount of time that the transceiver is active is determined by the length of time required to transmit or receive. To reduce advertising current consumption, embodiments herein limit the information, that is packaged within a BLE primary advertising packet, such as to limit the information to dynamical/primary (e.g., time critical) information. Separately, static/secondary information is provided in a scan request/response advertising packet. To communicate with the IMD, an external instrument performs an active scan during an initial device discovery phase before the external instrument establishes a full communications session with the IMD. After the initial device discovery phase, the external instrument then uses passive scans for further IMD updates to reduce IMD advertising power consumption. By way of example, a scan response, that is induced by an active scan, draws an additional 5% in overall current consumption in connection with a scan request data packet that is induced by a passive scan.

However, in connection with at least some embodiments, utilizing passive versus active scanning may still experience certain shortcomings. BLE is rapidly becoming a very commonly utilized wireless standard. Independent of IMD's and external instruments operating to communicate with IMD's, various electronic devices implement BLE enabled applications that utilize active scanning to discover any nearby devices. The potential exists that an IMD, in attempting to respond to these various BLE enabled applications, inadvertently increases the advertising power consumption of the IMD. Further, many BLE mobile platforms only implement active scanning which hinders the further saving from selective choice of advertising packets to reduce power consumption. Embodiments herein overcome the disadvantage of conventional BLE mobile platforms that do not readily enable the application program interface (API) to select/switch between active and passive scanning.

Further, embodiments herein address concerns in connection with malicious hackers that may attempt to utilize scan request to drain a battery of an IMD and thereby impact the longevity of the IMD. Embodiments herein provide methods and systems that manage device discovery and power consumption, and more specifically that provide countermeasures against undesirable active scan attacks while still allowing an IMD to determine an identity of an authorized external instrument in a scan response and establish a communication session therewith. In accordance with embodiments herein, a device discovery procedure mitigates effects of BLE active scan attacks from malicious hackers and other prevalent BLE Mobile Apps. Embodiments herein utilize the link layer advertising filter policy in the IMD to stop the IMD from responding to scan requests, meanwhile allowing a short connection period for the external instrument to retrieve the IMD information necessary to identify an IMD of interest.

The term "advertising policy", as used herein, refers to a set of rules that govern the communication, information, and data transmitted to and received by an electronic device in connection with advertising packets using a wireless Bluetooth communication protocol. Among other things, the advertising policy directs how the electronic device processes incoming scan requests (from separate device) that are received in response to an advertisement packet sent by the electronic device. Additionally, the advertising policy directs how the electronic device uses device identifiers, unique identifiers, advertising filters, look-up tables, and the like to establish communication sessions utilizing wireless Bluetooth communication protocol between two electric devices, including between an IMD and an external device such as an EI.

The term "approved device list", as used herein, refers to a list stored on an IMD and utilized by the IMD in connection with implementing advertising policies. The approved device list includes unique identifiers for implantable and/or external devices, with which the IMD is authorized to respond to scan requests.

The term "independent", as used herein, refers to an operation that is not dependent to or related to another operation. In the context of this disclosure, a communication session between and IMD and an authorized external device is established without utilizing a scan request packet from an external device, or being dependent on and IMD responding to the scan request data packet from an external device. Instead, in one example, the communication session is established utilizing a connection channel as a result of a connection request data packet from the external device. While advertising data packets can be transmitted from the IMD to the authorized external device, and include a unique identifier that is utilized by the authorized external device to prompt or result in a connection request data packet being transmitted through the connection channel, the operation of establishing the subsequent communication session is done only by a connection request data packet through the connection channel separate and without relation or dependence on a scan request data packet from the authorized external device through the scanning channel.

FIG. 1 illustrates a simplified block diagram of a system 100 operated in accordance with embodiments herein. The system 100 includes one or more IMD 101 and one or more external instrument (EI) 201 (e.g., table computer, smart phone, smart watch, laptop, and/or the like) that are configured to communicate with one another wirelessly over a communications link 140.

The IMD 101 is implanted within a patient 106 (e.g., proximate to and/or within a heart 103, proximate to the spinal cord). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference. Additionally or alternatively, the IMD 101 may be a leadless monitor, examples of which are disclosed in U.S. patent application Ser. No. 15/084,373, filed Mar. 29, 2016, entitled, "METHOD AND SYSTEM TO DISCRIMINATE RHYTHM PATTERNS IN CARDIAC ACTIVITY," which is expressly incorporated herein by reference.

Figure 2:
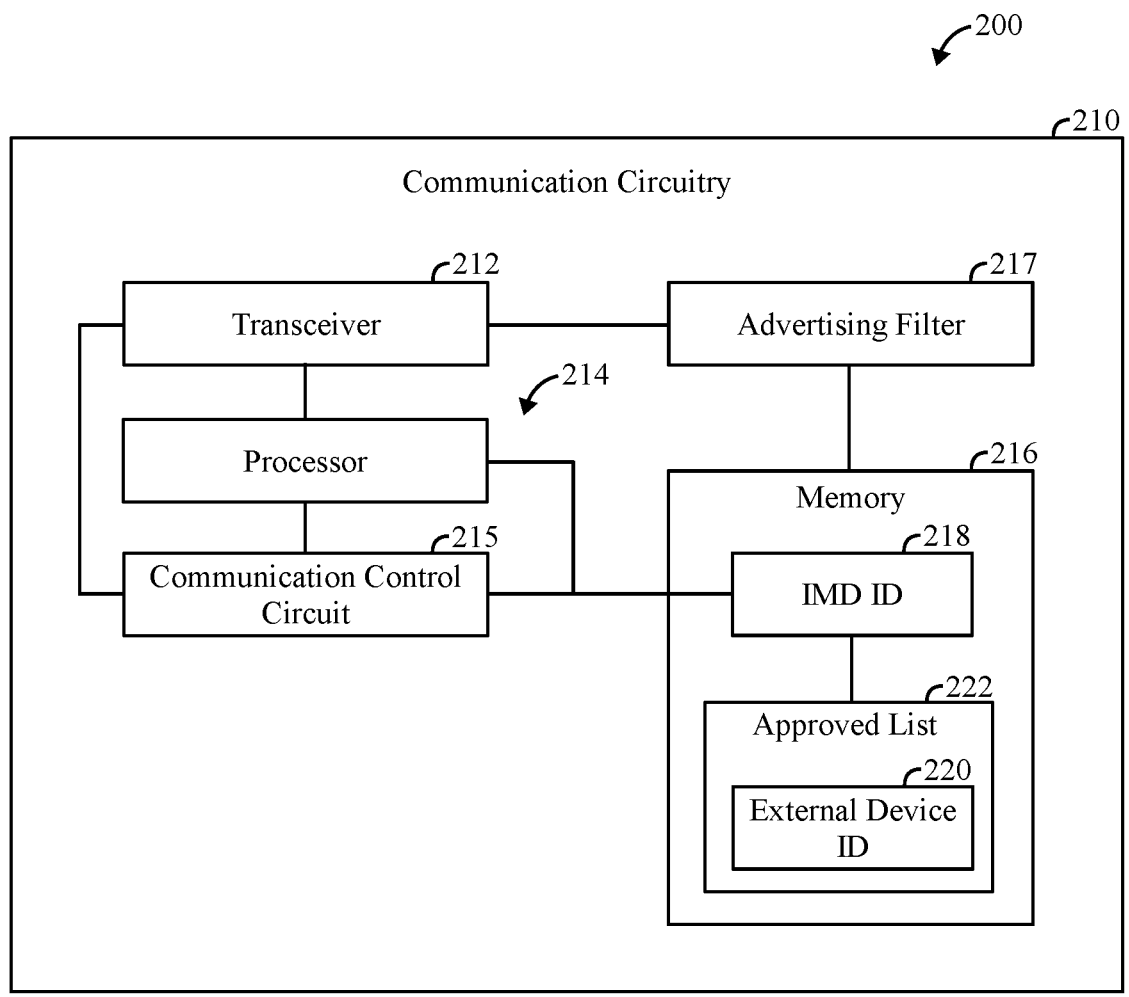
FIG. 2 illustrates a block diagram of communication circuitry operated in accordance with embodiments herein.

FIG. 2 illustrates a block diagram of a communication circuitry 200 of an IMD that in one example is the IMD 101 of FIG. 1. The components described herein can include or represent hardware and software instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. Additionally or alternatively, the components may be hard-wired logic circuits.

The communication circuitry 200 is within the housing 210 of an IMD. The housing 210 is often referred to as the "can", "case" or "case electrode" and may be programmably selected to act as the return electrode for all "unipolar" modes. The housing 210 may further be used as a return electrode alone or in combination with one or more of the coil electrodes for shocking purposes. The housing 210 further includes a connector (not shown) having a plurality of terminals. The terminals may be configured to be coupled to different types of electrodes and leads. In one example embodiment the IMD is a pacemaker.

The communication circuitry 200 is configured to manage the communication link between the IMD 101 and external devices. In one example the communication circuitry 200 may be configured to handle and/or manage the bi-directional communication link 140 between the IMD 101 and the EI 201. In one example the communication circuitry 200 is an RF circuit.

In another example the communication circuitry 200 includes a transponder that transmits signals and a receiver that receives signals. In yet another example, the communication circuitry 200 includes a transceiver 212 (TX/RX) that both transmits signals and receives signals. Specifically, a transceiver includes both a transponder and a receiver. As explained herein, the communication circuitry 200 transmits, among other things, advertising notices in accordance with one or more advertising schedules. The transceiver 212 is tuned to communicate with external devices, including the EI 201 over one or more frequency bands and in accordance with a corresponding protocol. The transceiver 212 may include one or more transmitters/transponders, receivers, and/or transceivers. Optionally, the communication circuitry 200 may be electrically coupled to an antenna (not shown). For example, an antenna may be provided within a header of an IMD as one example. As another example, electrodes on or coupled to the IMD may be utilized to convey the wireless communication signals. The communication circuitry 200 also scans for connection request data packets from external devices. In one example the external device is the EI 201 of FIG. 1.

The communication circuitry 200 also includes one or more processors 214 including a communication control processor 215, a local memory 216, and an advertising filter 217 all of which may be implemented on a common circuit board, within a common subsystem or within a common integrated circuit. Specifically, the communication circuitry 200 is in communication with other circuits, components, and modules of the IMD 101 including controller circuit, and IMD central memory 216. The communication control processor 215 may support one or more wireless communication protocols while communicating with an external device such as the EI 201, such as Bluetooth low energy, Bluetooth, Medical Implant Communication Service (MICS), and/or the like.

The memory 216 stores instructions implemented by the communication control processor 215. The memory 216 may also store the IMD identification (ID) 218, such as a unique identifier, that is assigned at the time of manufacture or program at a later time therein. The memory 216 may also store the external device IDs 220, that are received in both scanning request and connection request data packets. Additionally, protocol firmware may be stored in memory 216, which is accessed by the communication control processor 215. The protocol firmware provides the wireless protocol syntax for the communication control processor 215 to assemble data packets, advertisement notices, connection request data packets, connection responses, establish communication links, such as communication 140, and/or partition data received from an external device, such as EI 201.

The advertising filter 217 includes an advertising policy to determine when the IMD should respond to a scan request data packet from an external device. In one example the scan request data packet is any data packet transmitted by an external device through a scanning channel to be received by the transceiver 212. In another example the scan request data packet includes a device identifier. Specifically, the advertising filter 217 based on a rule set determines if a scan request data packet is from an authorized external device. In one example, the external device IDs 220 are on an approved device list 222 that is a list of device identifications (IDs) of authorized external devices. In an example, the approved device list 222 is within a look-up table. In another example, the IMD ID is the only device ID stored on the approved device list 222 to ensure no response signals are transmitted as a result of filter policy in connection with a desired channel. Therefore, based on determinations made by the advertising filter 217, the one or more processors deny the transmission of a response to the scan request data packet.

Figure 3:
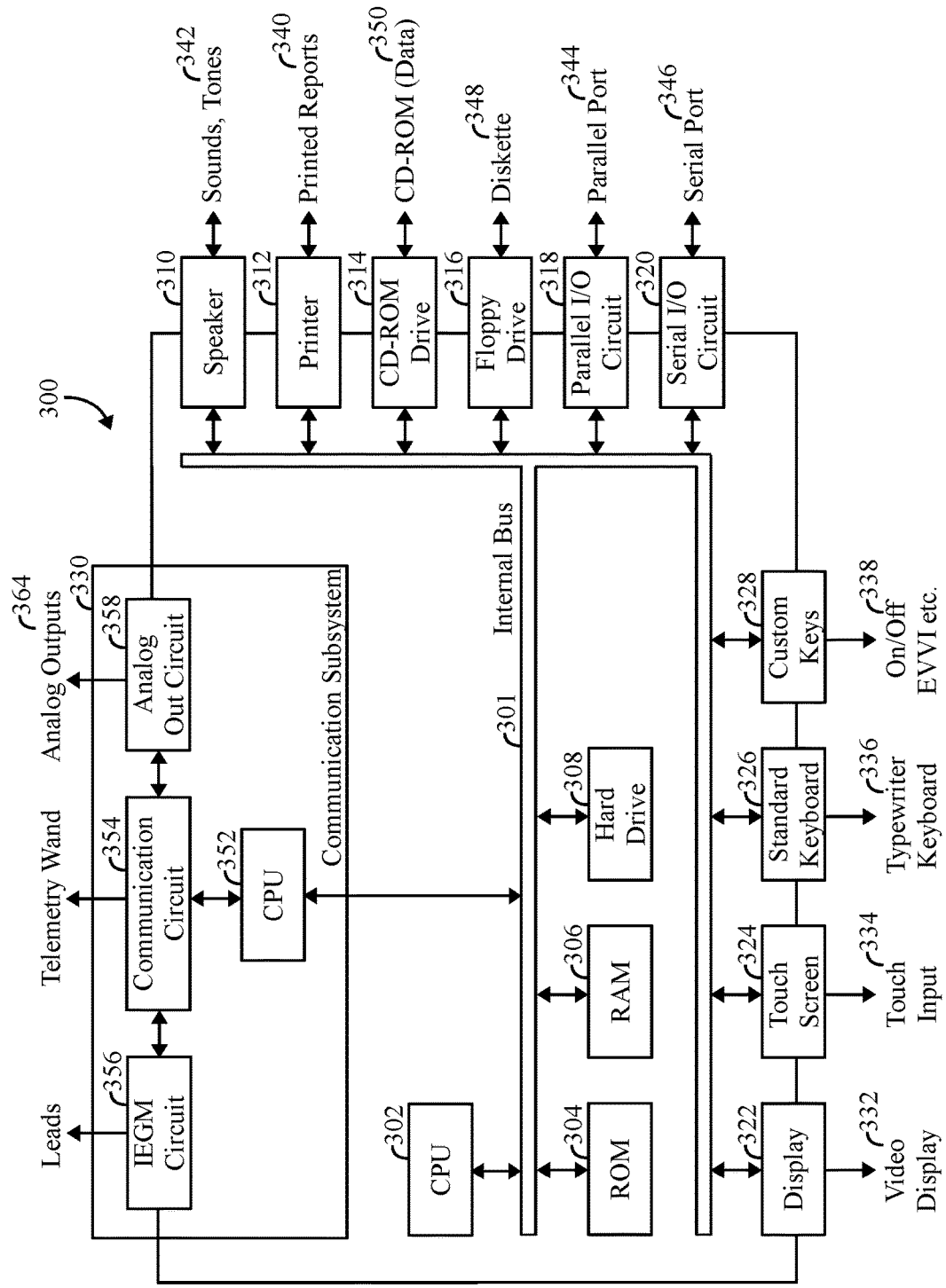
FIG. 3 illustrates a block diagram of an external instrument operated in accordance with embodiments herein.

FIG. 3 illustrates a functional block diagram of an external device 300 that is operated in accordance with embodiments herein. In one example the external device 300 is EI 201 of FIG. 1. The external device may be a workstation, a portable computer, a tablet computer, a smart watch, an IMD programmer, a PDA, a cell phone and/or the like. The external device 300 may include an internal bus 301 that may connect/interface with a Central Processing Unit ("CPU") 302, ROM 304, RAM 306, a hard drive 308, a speaker 310, a printer 312, a CD-ROM drive 314, a floppy drive 316, a parallel I/O circuit 318, a serial I/O circuit 320, the display 322, a touchscreen 324, a standard keyboard 326, custom keys 328, and an communication subsystem 330 that in one example is an RF subsystem. The internal bus 301 is an address/data bus that transfers information between the various components described herein. The hard drive 308 may store operational programs as well as data, such as stimulation waveform templates and detection thresholds.

The CPU 302 typically includes one or more microprocessors, one or more micro-controllers, or equivalent control circuitry, designed specifically to control interfacing with the external device and with an IMD, such as IMD 101 of FIG. 1. The CPU 302 performs the operations described herein by the external instrument including but not limited to the registration process and operations for establishing a secure communications connection with an IMD.

The CPU 302 may include RAM or ROM memory, logic and timing circuitry, state machine circuitry, and I/O circuitry to interface with an IMD. The display 322 (e.g., may be connected to the video display 332). The display 322 displays various information related to the processes described herein. The touchscreen 324 may display graphic information relating to the IMD 101 and include a graphical user interface. The graphical user interface may include graphical icons, scroll bars, buttons, and the like which may receive or detect user or touch inputs 334 for the external device 300 when selections are made by the user. Optionally the touchscreen 324 may be integrated with the display 322. The keyboard 326 (e.g., a typewriter keyboard 336) allows the user to enter data to the displayed fields, as well as interface with the communication subsystem 330. Furthermore, custom keys 328 turn on/off 338 (e.g., EVVI) the external device 300. The printer 312 prints copies of reports 340 for a physician to review or to be placed in a patient file, and the speaker 310 provides an audible warning (e.g., sounds and tones 342) to the user. The parallel I/O circuit 318 interfaces with a parallel port 344. The serial I/O circuit 320 interfaces with a serial port 346. The floppy drive 316 accepts diskettes 348. Optionally, the serial I/O port may be coupled to a USB port or other interface capable of communicating with a USB device such as a memory stick. The CD-ROM drive 314 accepts CD ROMs 350. One or more scanning schedules are stored in the RAM 306, ROM 304, on a CD ROM 350, or elsewhere.

The communication subsystem 330 includes a central processing unit (CPU) 352 in electrical communication with a communication circuit 354, which may communicate with both the memory 356 and an analog out circuit 358. The analog out circuit 358 includes communication circuits to communicate with analog outputs 364. The external device 300 may wirelessly communicate with an IMD and utilize protocols, such as Bluetooth, Bluetooth low energy, MICS, and/or the like. For example, the memory 356, ROM 304, and/or RAM 306 may include Protocol firmware, which is accessed by the CPU 352 and/or 302. The protocol firmware provides the wireless protocol syntax for the CPU 352 and/or 302 to assemble data packets, establish communication links, such as communication link 140, and/or partition data received from the IMD. The communication subsystem 330 and CPU 352 enter scanning states and establish communication sessions as described herein.

Process for Device Discovery Countermeasures

The scan response blocking control for the IMD starts with utilizing a link layer advertising filter. Specifically, the advertising policy of the IMD is set such that the IMD only processes scan request data packets associated with, or on a white list, or within a look-up table. In one example, the white list is configured with only the unique identifier of the IMD itself so that the IMD blocks all scan responses from third party devices while still allowing connection request data packets from an authorized external device. Specifically, a connection channel remains open to receive connection request data packets from all devices, including authorized external devices such that once the authorized external device verifies the IMD's advertisement, the connection request data packet may be transmitted. Therefore, the number of devices to which the IMD responds is limited, increasing security and decreasing power consumption.

Figure 4:
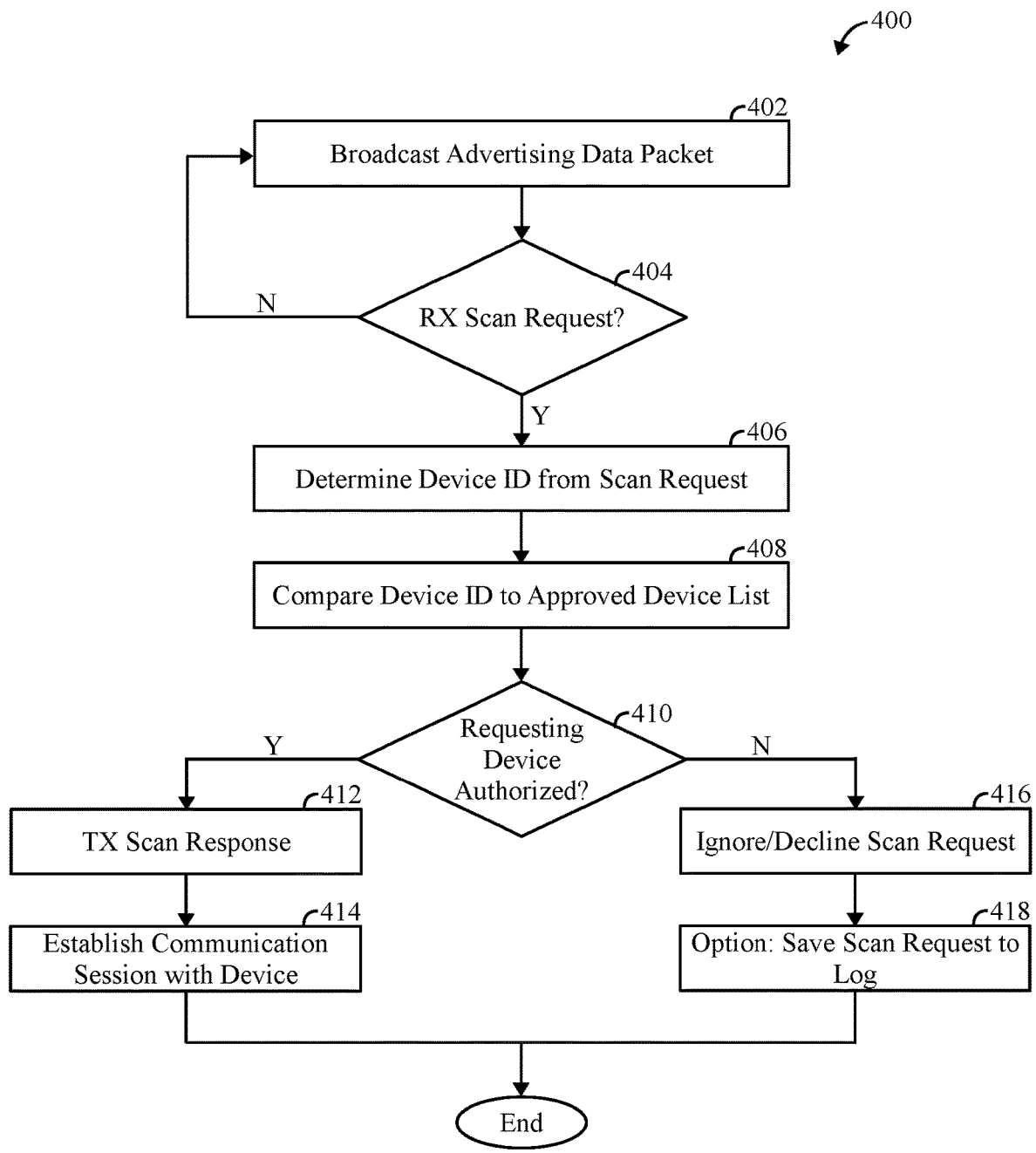
FIG. 4 illustrates a block flow chart of a method in accordance with embodiments herein.

FIG. 4 illustrates a process for blocking unauthorized scan responses utilizing the link layer advertising filter 400 in accordance with embodiments herein. At 402, one or more processors of the IMD broadcasts advertising data packets. For example, a communication circuitry 200 (FIG. 2) may include a transceiver that transmits advertising data packets in one or more scanning channels. In one example, the advertising data packets include a unique identifier that is associated with an IMD such as IMD 101. In another example the unique identifier is a universal unique identifier (UUID) that is known to authorized external devices such as the EI 201.

At 404, the communication circuitry 200 determines whether a scan request data packet has been received. In one example a transceiver of the communication circuitry 200 receives the scan request data packet through a scanning channel. In another example the scan request data packet is transmitted by a remote, or unauthorized external device not associated or related to the patient or IMD. In one example, the remote external device belongs to a hacker attempting to receive information from the IMD. When a scan request data packet is not received, flow returns to 402 where the next advertising data packet is transmitted in a predetermined periodic manner during predetermined intervals. In one example an advertising data packet is transmitted every 5 seconds until a connection request data packet is received by the communication circuitry 200. In another example, an advertising data packet is transmitted every 2 seconds. In yet another example the advertising data packet is transmitted periodically in a range between every 1 second and 10 seconds.

At 404, when a scan request data packet is received, flow moves to 406. At 406-410, the IMD applies an advertising filter 217 at the link layer. For example, at 406, one or more processors of the IMD unpack the scan request data packets and determine, among other things, a device identifier (ID) for the external device that transmitted the scan request data packet. In one example, each device ID received in each scan request data packet of a plurality of scan request data packets is inputted into a log or report that is recorded and attached to a communication to a user such as a clinician. The communication can include an email, print-out, instant message, and the like. In this manner, a list of suspicious devices may be created in an attempt to identify hackers attempting to steal information and drain battery life of the IMD.

At 408, the one or more processors compare the device ID to historical data such as an approved device list 222. In one example, the approved device list 222 is a white list. In yet another example the approved device list 222 is a look-up table where the device ID is compared to each device ID listed within the look-up table. Specifically, in one embodiment, only the device ID of the IMD itself is listed on the device list, or in the look-up table. Additionally or alternatively, no device IDs are on the device list, or within the look-up table. In this manner, no scan request data packets are authorized, and all are filtered out of the system. In another example, multiple device IDs from corresponding multiple scan request data packets from corresponding multiple external devices. Consequently, the advertising filter 217 and corresponding policy prevents a response signal from being transmitted from the IMD to an external device. Thus, responding to an external device operated by a hacker is prevented.

At 410, the one or more processors determine whether the device ID from the scan request data packet is on the approved device list 222, thereby indicating that the requesting device is authorized. For example, the operations at 406-410 may be implemented by the communication circuitry 200. The communication circuitry 200 may include, or be coupled to one or more processors that implement an advertisement filter 217 that is configured to implement advertising policy in accordance with the operations at 406-410. Among other things, the advertising policy may define when and to what extent the IMD responds to requests, such as a scan request from an external device. The transceiver 212 broadcasts (at 402) advertisement data in the advertisement data packet which can be picked up by any BLE enabled scanning device. In the event that a BLE enabled scanning device responds with a scan request data packet to request more data from the IMD (advertiser), the IMD applies one or more filter policies. As one example, a filter policy may indicate that the IMD is only permitted to respond to scan request data packets from third-party devices that are on an approved device list 222 (e.g., white list).

At 410, when the one or more processors determine that a scan request data packet is received from a device on the approved device list 222, flow moves to 412. At 412, the transceiver 212 responds by transmitting an appropriate scan response data packet. Accordingly, the IMD (as the advertiser) can choose to send scan response data only to certain devices, namely authorized devices contained on the white list. Additionally or alternatively, as described above, the approved device list 222 can include no devices, or only the IMD itself, preventing response signals being transmitted through the scanning channel.

Thereafter, at 414, when an approved device is provided, the communication circuitry 200 communicates with the external device to establish a communication session with the external device independent of a scan request packet from an external device. In particular, the communication session between the IMD and external device is established independent of the scan request packet from the external device because the scanning channel, and specifically a scan request data packet from the external device, is not utilized by the external device (that is an authorized external device) and IMD in establishing the communication session. Instead, only the connection channel through a connection request data packet is used. In one example, the IMD transmits a unique identifier in an advertising data packet through the scanning channel and this unique identifier is utilized to prompt or cause the external device, or authorized external device, to transmit the connection request data packet. Still, the establishment of the communication session is not as a result of the IMD responding to a scan request data packet transmitted by the external device. In this manner, the establishment of the communication session is independent of a scan request data packet. Consequently, because the IMD establishes the communication session independent to a scan request data packet, and responses to scan request data packets form external devices are not required, and battery life of the IMD is saved. Specifically, the connect channel is already continually searching for and responding to connection requests, thus, by utilizing this channel to establish the communication session, reduced battery use compared to periodically searching and responding to a scan request data packets through the scan request channel is realized.

Alternatively, at 410, when the one or more processors determine that the scan request data packet was received from an external device that is not on the approved device list 222 (also referred to as an unauthorized external device), flow moves to 416.

At 416, the one or more processors deny transmission of the scan request data packet from the transceiver when the advertising filter determines that the scan request data packet is from an unauthorized external device. Specifically, the unauthorized external device does not have a communication session established with the IMD and the one or more processors denies the transmission of a scan request data packet or any information that could be received by the unauthorized external device from the IMD to result in a communication session being established. In one example the one or more processors ignore a received scan request data packet from an external device upon determining that the scan request data packet is not on the approved device list 222. Alternatively, the one or more processors block transmission of the scan request data packet upon determination that the scan request data packet was received from a device not on the approved device list 222. In yet another example, the one or more processors decline to transmit a response to a scan request data packet from an external device upon determining that the scan request data packet is not on the approved device list 222. As a result of denying a response transmission, the unauthorized external device is unable to establish a communication session with the IMD based on a response to a scan request data packet transmitted by the IMD.

Optionally, at 418, when a scan request data packet is received from an unauthorized device, the one or more processors may record a log of the scan request data packet along with a device ID for the unauthorized device. The log of unauthorized scan request data packet may be later downloaded, inputted into a log or report for attachment to a communication, and the like such as in connection with analysis to identify malicious attacks against the IMD. Therefore, in an example wherein the IMD is the only approved device in the look-up table, the IMD simply does not respond to any scan requests, preventing consumption of currently, and preventing responses to nefarious individuals.

Figure 5:
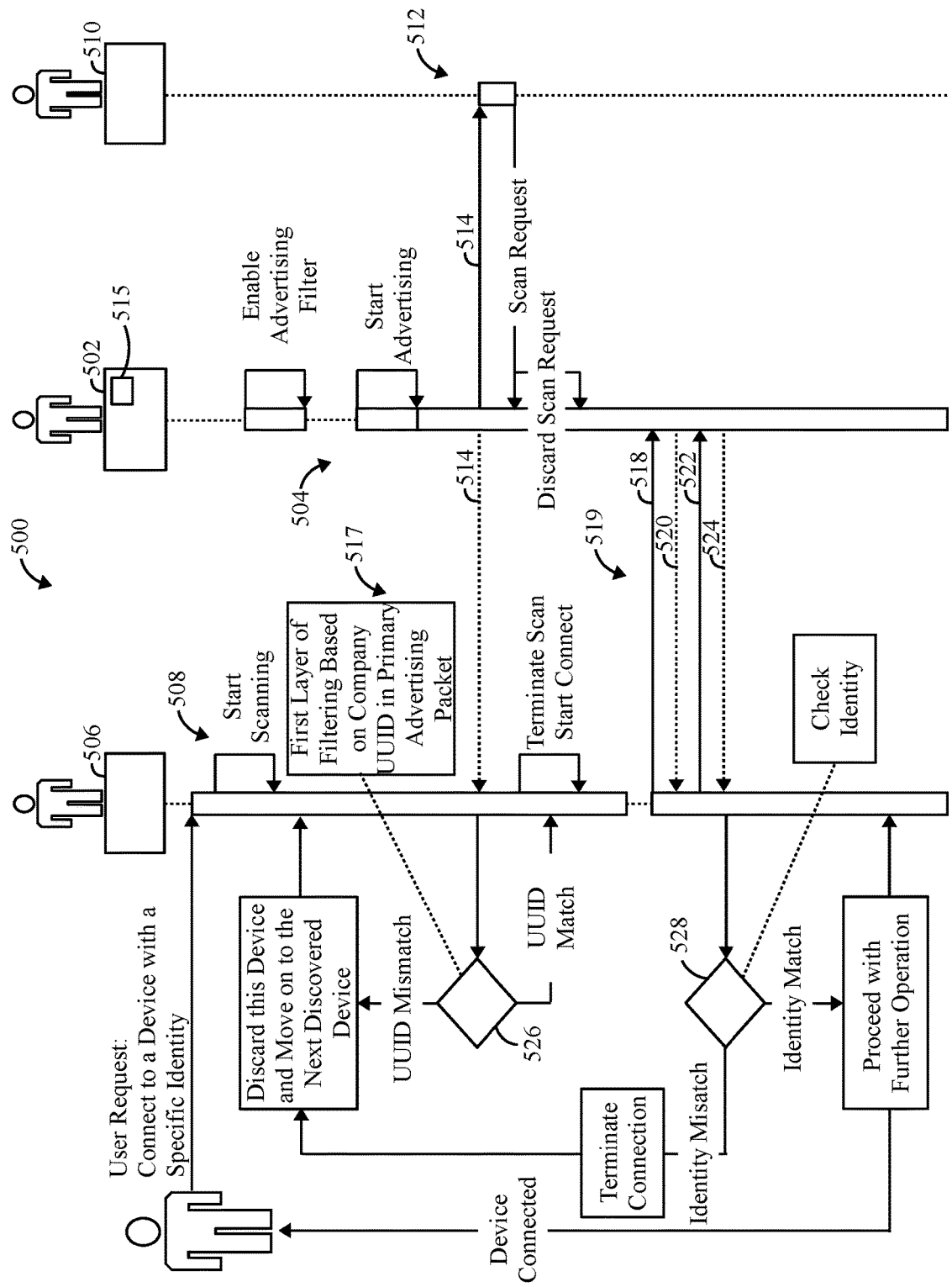
FIG. 5 illustrates a simplified block diagram of a communication system operated in accordance with embodiments herein.

FIG. 5 illustrates an example schematic block diagram of a communication link system 500 utilizing the IMD 101 of FIGS. 1-2 and an authorized external device such as the IE of FIGS. 1 and 3, wherein the IMD 101 utilizes the methodology of FIG. 4 to prevent third party unauthorized external devices from gaining access to the IMD. The communication link system 500 includes an IMD 502 with an IMD communication link 504, an authorized external device 506 with an authorized communication link 508, and an unauthorized external device 510 with an unauthorized communication link 512.

The IMD 502 in one example is IMD 101 of FIGS. 1-2. The IMD communication link 504 in an example operates as described in the method of FIG. 4. Specifically, the IMD 502 transmits advertising data packets 514 that include a unique identifier for receipt by the authorized external device 506 at the authorized communication link 508 through one or more scanning channels 517. In one example the unique identifier is a universal unique identifier (UUID).

The IMD 502 includes an advertising filter 515 that prevents response signals from being transmitted in response to scan request data packets 516 received by a transceiver of the IMD 502 through a scanning channel 517. Such scan request data packets include scan request data packets from the authorized external device 506 and the unauthorized external device 510. In one example the advertising filter includes a look-up table that only contains device IDs associated with the IMD 502 such that the IMD 502 only transmits a response signal to scan request data packets from authorized external devices 506. Additionally or alternatively, in one example no scan request data packets are accepted by an advertising filter 515.

Meanwhile, the IMD 502 communication link 504 continues to accept all connection request data packets 518 through a connection channel 519. Thus, the transceiver of the IMD 502 transmits response signals 520 responsive to receiving a connection request data packet 518 through the connection channel 519. After transmitting a response signal 520 the transceiver of the IMD 502 is configured to receive request signals 522 and transmit an IMD data packet 524 that can include identification data in response in order to establish a communication session with the authorized external device 506 through which the IMD 502 shares and communicate health information to the authorized external device 506.

The authorized external device 506 includes the authorized communication link 508 that receives the advertising data packets 514 from the IMD 502. The authorized EI 506 includes an advertising filter 526 and an identification filter 528. The advertising filter 526 verifies that the advertising data packet 514 received from the IMD 502 is from a desired IMD 502. In one example, the advertising filter 526 includes a look-up table that includes the unique identifier transmitted in the advertising data packet 514 of the IMD 502. If the unique identifier matches with the unique identifier within the look-up table the authorized EI 506 transmits a connection request data packet 518 that is received by the IMD communication link 504. Once received, the IMD 502 automatically accepts the connection request data packet 518 and transmits the response signal 520 that is received by a receiver module of the authorized external device 506. The authorized external device 506 with a transceiver then transmits a request signal 522 for the identity of the IMD 502.

The authorized external device 506, then at the transceiver, receives an IMD data packet 524 that includes a device identification. In one example, the device identification is a unique identifier associated with the IMD 502. In one example, the unique identifier is the same unique identifier that is transmitted with the transmitted advertising data packet 514. In another example the unique identifier is different than the unique identifier that is transmitted with the transmitted advertising data packet. Once the transceiver of the authorized EI receives the identification data, the identification filter 528 determines if the transmitted IMD data packet 524 is being transmitted by an appropriate or authorized IMD 502. If not, communication between the IMD 502 and authorized EI would cease. Alternatively, once confirmed communication between the IMD 502 and authorized external device 506 transpires. Thus, communication occurs without use of a scanning channel, reducing current consumption.

The unauthorized EI 510, meanwhile also receives the transmitted advertising data packet 514. In response, the unauthorized EI 510 does not have the unique identifier information, and instead simply transmits an unauthorized scan request data packet 516. In response to receiving the unauthorized scan request data packet, the advertising filter 526 prevents a response by the IMD 502 and no further action by the IMD 502 is undertaken. Therefore, hacking from a nefarious individual utilizing an unauthorized EI 510 is prevented, improving security.

Figure 6:
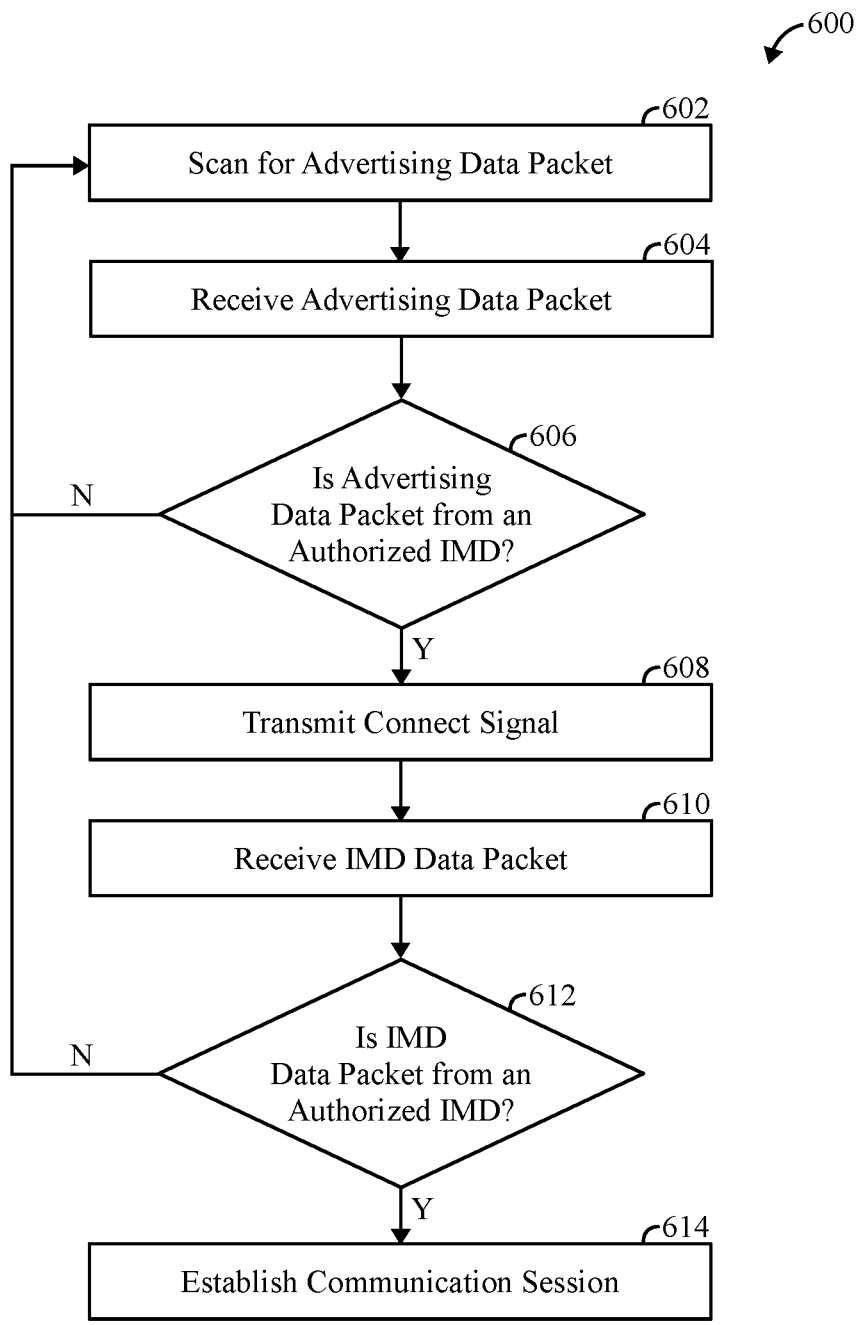
FIG. 6 illustrates a block flow chart of a method in accordance with embodiments herein.

FIG. 6 illustrates a block flow diagram of the method 600 of identifying IMD 502 by the authorized external device 506. At 602, the authorized external device 506 repeatedly scans for advertising data packets. In one example, the authorized EI scans for a predetermined interval, or amount of time, and then rests for a predetermined interval, or amount of time in a cycle. Alternatively, the authorized EI does not stop scanning. At 604, the authorized EI receives an advertising data packet that was transmitted by the IMD 502. In one example the advertising data packet includes a unique identifier that in one embodiment is a universal unique identifier. At 606, an advertising filter of the authorized external device 506 determines if the advertising data packet is from an authorized, or approved IMD. If no, the authorized EI continues to scan, repeating 602-606 until identifying an advertising data packet from an authorized or approved IMD.

Thus, at 606, yes, then at 608 the authorized external device 506 transmits a connection request data packet 518, through a connect channel to be received by the IMD 502. At 610, responsive to receiving a response signal 520 from the IMD based on the connection request data packet 518, the authorized external device 506 transmits a request signal 522 to receive information and data from the IMD. At 612, the authorized external device 506 receives an IMD data packet 524 that includes a unique identifier associated or related to the IMD 502.

At 614 a determination is made regarding whether the received IMD packet 524 was transmitted from an appropriate, or authorized IMD 502. In one example, a look-up table is utilized to determine if the unique identifier matches a unique identifier in the look-up table. If the IMD packet 524 was not transmitted from an authorized, or appropriate IMD, then the authorized IMD 502 does not respond to the IMD packet 524 and begins scanning for advertising data packets 514 at 602. If at 614, the IMD packet is transmitted from an appropriate, or authorized IMD 502, at 616 a communication session is established and communication between the authorized external device 506 and IMD 502 continues and information is shared.

Thus, provided is a discovery procedure for an authorized external device 506 that begins with a scanning procedure. Although only primary advertising packets are returned due to the advertising policy enabled in the device, the authorized external device 506 can still use a unique identifier such as a company's UUID that is within a primary advertising packet 514 to perform a filtering process for devices of interest. Once the first filtering is done and because the advertising filter policy in the IMD 502 does not block connect requests, the authorized external device 506 can proceed to connecting to the potential IMD 502, following a predefined procedure to find the IMD's identity in lieu of getting it from the scan response. The authorized external device 506 can then in one example establish the relationship between IMD identity and Bluetooth identity for subsequent connections. Therefore, battery life is saved while hackers are prevented from attaching the scan channel. Additionally, a session establish protocol may be utilized to provide denial of service for illegitimate users. Similarly, the IMD 502 can still temporarily disable advertising policy with other security means, e.g., magnet and/or inductive triggered events, to allow faster device discovery procedure through active scanning for a short period of time before establishing a relationship with the authorized external device 506. Afterwards, the IMD 502 goes back to limited mode advertising to block scan request data packets. Thus, security is enhanced while battery usage at the IMD 502 is minimized.

Closing Statement

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. An external device (ED) for communicating with an implantable medical device (IMD), comprising:
    a transceiver, within the ED, configured to scan for an advertising data packet;
    memory, within the ED, configured to store program instructions and an authorized IMD list; and
    one or more processors, within the ED, configured to execute the program instructions to:
    identify an identifier (ID) from the advertising data packet;
    apply a filter to determine when the advertising data packet is from an authorized IMD based on the ID, wherein the filter determines when the advertising data packet is from an authorized IMD based on the ID and the authorized IMD list, wherein the filter does not block connection requests;
    based on the determination by the filter, transmit a connection request data packet when the filter determines that the advertising data packet is from the authorized IMD; and
    establish a communication session with the authorized IMD,
    wherein the transceiver is further configured to transmit a scan request data packet to the IMD, and the one or more processors are further configured to establish the communication session with the authorized IMD independent of the scan request data packet.

2. The device of claim 1, wherein the transceiver is further configured to transmit the scan request data packet before receiving the advertising data packet.

3. The device of claim 1, wherein the advertising data packet broadcast from the IMD includes a universal unique identifier (UUID) of the IMD.

4. The device of claim 1, wherein the ID represents a unique identifier for the IMD.

5. The device of claim 1, wherein the advertising data packet is from one of a cardiac monitoring device, pacemaker, cardioverter, cardiac rhythm management device, defibrillator, neurostimulator, leadless monitoring device, or leadless pacemaker.

6. The device of claim 1, wherein the communications session is established using a Bluetooth low energy (BLE) protocol, and the filter represents a BLE link layer advertising filter.

7. The device of claim 1, wherein the external device represents one of a table computer, smart phone, smart watch, laptop, or programmer device.

8. An external device (ED) for communicating with an implantable medical device (IMD), comprising:
    a transceiver, within the ED, configured to scan for an advertising data packet;
    memory, within the ED, configured to store program instructions and an authorized IMD list; and
    one or more processors, within the ED, configured to execute the program instructions to:
    identify an identifier (ID) from the advertising data packet;
    apply a filter to determine when the advertising data packet is from an authorized IMD based on the ID, wherein the filter determines when the advertising data packet is from an authorized IMD based on the ID and the authorized IMD list, wherein the filter does not block connection requests;

based on the determination by the filter, transmit a connection request data packet when the filter determines that the advertising data packet is from the authorized IMD; and establish a communication session with the authorized IMD, wherein the one or more processors are further configured to execute the program instruction to:

establish the communication session with the authorized IMD based on a response from the IMD to the connection request data packet.

9. The device of claim 8, wherein the response from the IMD includes a universal unique identifier related to the IMD.

10. A method, the method comprising:

under control of one or more processors of an external device (ED), scanning, at the ED, for an advertising data packet broadcast from an implantable medical device utilizing a communication protocol;

identifying an identifier (ID) from the advertising data packet;

applying a filter, at the ED, to determine when the advertising data packet is from an authorized IMD based on the ID, wherein the filter determines when the advertising data packet is from an authorized IMD based on the ID and an approved IMD list, wherein the filter does not block connection requests;

based on the determination by the filter, transmitting a connection request data packet from the ED when the filter determines that the advertising data packet is from the authorized IMD;

establishing a communication session with the authorized IMD;

transmitting a scan request data packet from the ED; and establishing the communication session with the authorized IMD independent of the scan request data packet.

11. The method of claim 10, further comprising transmitting the scan request data packet before receiving the advertising data packet.

12. The method of claim 10, wherein the ID represents a unique identifier for the IMD.

13. The method of claim 10, wherein the advertising data packet is from one of a cardiac monitoring device, pacemaker, cardioverter, cardiac rhythm management device, defibrillator, neurostimulator, leadless monitoring device, or leadless pacemaker.

14. The method of claim 10, wherein the communications session is established using a Bluetooth low energy (BLE) protocol, and the filter represents a BLE link layer advertising filter.

15. The method of claim 10, wherein the one or more wireless communication protocols include a Bluetooth low energy (BLE) protocol, and the advertising filter is applied at a BLE link layer.

16. The method of claim 10, further comprising transmitting the connection request data packet after transmitting a scan request data packet and after the filter is applied.

17. A method, the method comprising:

under control of one or more processors of an external device (ED), scanning, at the ED, for an advertising data packet broadcast from an implantable medical device utilizing a communication protocol;

identifying an identifier (ID) from the advertising data packet;

applying a filter, at the ED, to determine when the advertising data packet is from an authorized IMD based on the ID, wherein the filter determines when the advertising data packet is from an authorized IMD based on the ID and an approved IMD list, wherein the filter does not block connection requests;

based on the determination by the filter, transmitting a connection request data packet from the ED when the filter determines that the advertising data packet is from the authorized IMD;

establishing a communication session with the authorized IMD; and establishing the communication session with the authorized IMD based on a response from the IMD to the connection request data packet.

18. The method of claim 17, wherein the response from the IMD includes a universal unique identifier related to the IMD.

* * * * *